(12) United States Patent
Healy et al.

(10) Patent No.: US 6,451,582 B1
(45) Date of Patent: Sep. 17, 2002

(54) STAPHYLOCOCCUS STRAINS COMPRISING AN INDUCIBLE GENE ENCODING AN RNA POLYMERASE SPECIFICITY FACTOR

(75) Inventors: Judith M. Healy; C. Richard Wobbe, both of Lexington; Patricia Carroll, Watertown; Jason Thresher, Somerville, all of MA (US)

(73) Assignee: Anadys Pharmaceuticals, Inc, San Diego, CA (US)

( * ) Notice: Subject to any disclaimer, the term of this patent is extended or adjusted under 35 U.S.C. 154(b) by 0 days.

(21) Appl. No.: 09/501,838

(22) Filed: Feb. 10, 2000

(51) Int. Cl.⁷ .......................... C12N 1/20; C12N 15/74; C07H 21/04
(52) U.S. Cl. .................... 435/252.3; 435/471; 435/477; 435/481; 536/23.1; 536/24.1
(58) Field of Search ............................. 435/252.3, 477, 435/471, 481; 536/23.1, 24.1

(56) References Cited

U.S. PATENT DOCUMENTS

| | | |
|---|---|---|
| 5,585,277 A | 12/1996 | Bowie et al. |
| 5,679,582 A | 10/1997 | Bowie et al. |
| 6,027,932 A * | 2/2000 | Goldberg et al. ........... 435/245 |

OTHER PUBLICATIONS

Hicks et al. Molecular Microbiology. vol. 20, No. 1, pp. 201–212, 1996.*
Barthelemy et al., J. Virol. May 1987;61(5):1751–5.
Basheer et al., Nucleic Acids Res. Sep. 25, 1991;19(18):4921–4.
Henner DJ, Methods Enzymol. 1990;185:223–8.
Horinouchi et al., J Bacteriol. May 1982; 150(2):815–25.
Jaacks et al., J Bacteriol. Aug. 1989;171(8):4121–9.
Kreiswirth et al., Nature. Oct. 20–26, 1983;305(5936):709–12.
Schenk et al., FEMS Microbiol Lett. Jul. 1, 1992;73(1–2):133–8.

* cited by examiner

*Primary Examiner*—David Guzo
*Assistant Examiner*—Gerald G. Leffers, Jr.
(74) *Attorney, Agent, or Firm*—David R Preston & Associates; David Preston

(57) ABSTRACT

The present invention relates to a recombinant organism, and a bacterial strain such as Staphylococcus, and *S. aureus*, in particular. The organism has a regulatable gene for encoding an RNA polymerase specificity factor required for expression of at least one gene essential for growth of the organism. The regulatable gene is one which is responsive to an exogenous effector molecule, and may in particular be an inducer-responsive gene including an operator site, such as a lac operator, to which a repressor, such as a lacI-encoded repressor, is capable of binding. The regulatable gene may in particular be an IPTG responsive plaC allele.

14 Claims, 6 Drawing Sheets

Integrative Vector to Engineer Inducible Gene Expression

TTGACTTTATCTACAAGGTGTGGCATAATGTGTGGAATTGTGAGCGGATAACAATT
 -35                                -10           << lac operator >>

AAGCTTAACGAGGTGATCTAGAGTCGACGCCCGGGCGTCGACCTGCAGGCATGC
HindIII * rbs *        SalI   SrfI    SalI   PstI

**Depletion of *plaC*-Encoded Sigma Factor Cripples Growth of *S. aureus***

PlaC Expressed     PlaC Depleted

STAPHYLOCOCCUS STRAINS COMPRISING AN INDUCIBLE GENE ENCODING AN RNA POLYMERASE SPECIFICITY FACTOR

FIELD OF THE INVENTION

The present invention relates generally to genetically engineered organisms useful for screening pharmaceutical compounds having antimicrobial capability and, more particularly, to recombinant organisms in which the expression of an RNA polymerase specificity factor can be regulated. The present invention is more specifically directed to recombinant bacterial strains in which the expression of RNA polymerase σ subunit can be regulated by the addition of an exogenous effector molecule. In particular, the present invention relates to a new recombinant staphylococcal bacterial strain having an engineered inducer-responsive gene for regulating expression of RNA polymerase a subunit and methods for utilizing the same in high throughput screening to detect antimicrobial compounds pharmaceutically useful against staphylococcal bacteria.

BACKGROUND OF THE INVENTION

Numerous pathogenic organisms, such as *Staphylococcus aureus* ("*S. aureus*"), are responsible for infectious disease and health-related problems in humans and other animals throughout the United States and the world. As treatments are developed for combating a particular organism, such as treatments incorporating newly developed antibiotics and chemical compounds effective at eliminating existing strains of a particular organism, newer strains of such organisms emerge which are resistant to the existing treatments. Accordingly, there remains a constant need for the development of new ways for pharmaceutically combating pathogenic organisms.

Methods for combating an organism by interfering with genetic processes essential to survival and growth of the organism are becoming of increasing interest. In particular, researchers are directing their attention to chemical compounds which interfere with genetic transcription processes required for growth or continued existence of pathogenic organisms.

The expression of genetic information in an organism ultimately occurs via proteins, and particularly by enzymatic proteins which catalyze metabolic reactions. The flow of genetic information from DNA to protein occurs generally in two steps, termed "transcription" and "translation". Transcription is the first step in the flow of genetic information, whereby DNA-encoded genetic information is copied into RNA. The further conversion of RNA into protein occurs by the process of translation. A "gene" is broadly a region of DNA which encodes one protein, and the transcription-translation process of forming that protein is termed "expression" of the gene.

In particular, transcription involves the synthesis of an RNA chain representing one strand of a DNA duplex. Importantly, RNA synthesis is catalyzed by an enzyme known as RNA polymerase. Transcription begins when RNA polymerase binds to a special region at the beginning of a DNA gene known as a promoter site.

RNA polymerase is generally comprised of two components, a core enzyme and a specificity factor. The specificity factor is particularly concerned with recognition and binding of the enzyme to the promoter region of a particular gene or set of genes on a DNA template. While the core enzyme component of RNA polymerase has the ability to synthesize RNA on a DNA template, it cannot initiate transcription at the promoter site without an associated specificity factor. The function of the specificity factor, thus, is to insure that RNA polymerase binds in a stable manner to DNA only at appropriate promoter sites. Consequently, the specificity factor directs binding of RNA polymerase at cognate promoter sequences, thereby initiating expression of only those selected genes incorporating the cognate promoter sequences.

Accordingly, the expression of a particular gene or set of genes can be controlled by regulating production of a corresponding specificity factor. In particular, the expression of a particular gene or set of genes can be inhibited by blocking the associated specificity factor, thereby preventing the binding of RNA polymerase to the gene promoter sequences. As a result, an attractive target for the treatment of a pathogenic organism would be the discovery of chemical agents which block an RNA polymerase specificity factor required for the expression of a gene or set of genes essential for continued existence of the organism.

One particular pathogenic organism of concern is the bacterium *S. aureus*, which is an opportunistic human pathogen and is the primary cause of nosocomial bacterial infections in the United States. *S. aureus* is associated with a number of life threatening systemic illnesses, such as bacteremia/sepsis, toxic shock syndrome and toxic epidermal necrolysis, as well as common bacterial infections of the skin. The recent emergence of methicillin-resistant and vancomycin-resistant strains of *S. aureus* has focused renewed attention on the need for development of new classes of antibiotics to combat such bacterial strains. A promising way of pharmaceutically combating bacterial strains, including *S. aureus* and other staphylococcal strains, is to interfere with genetic transcription processes relating to growth of the bacteria.

As in other eubacteria, the RNA polymerase of *S. aureus* is composed of two components, the core enzyme and a specificity factor. The core enzyme has a subunit composition of ($\alpha_2\beta\beta'$). The $\beta$ and $\beta'$ subunits together make up the catalytic center of the enzyme while the $\alpha$ subunit is required for assembly of the core enzyme, as well as other functions in promoter recognition.

The specificity factor in *S. aureus* is one of several σ subunits or factors. The principle σ factor, encoded and expressed in *S. aureus* by the chromosomal gene plaC, is required for the expression of essential housekeeping genes required for bacterial growth. As a result, this σ factor is an attractive target for the discovery of chemical agents which possess antibacterial properties by binding with or blocking the σ factor function, since the blocking of or interfering with the σ factor function can prevent expression of these housekeeping genes and retard or prevent growth of the bacteria.

U.S. Pat. Nos. 5,585,277 and 5,679,582 to Bowie et al. disclose methods for screening chemical compounds for potential pharmaceutical or antimicrobial effectiveness. In particular, these patents teach methods for identifying possible therapeutic ligands which bind to target proteins. The methods of these patents may be useful in affinity-based assays for the initial identification of chemical compounds as in vitro inhibitors of an RNA polymerase and more specifically an RNA polymerase specificity factor, such as the primary σ subunit in staphylococcal bacteria. However, there remains a need in the art for screening methods, and recombinant organisms useful therein, which monitor the in vivo effects of chemical compounds on the growth and/or survival of a target organism. Specifically, there remains a need in the art for recombinant organisms, and production methods therefor, in which the production of an RNA polymerase specificity factor which encodes a gene essential for growth or continued existence of the organism can be specifically controlled for use in screening processes. In particular, there remains a need in the art for a staphylococcal bacterial strain in which the production of RNA polymerase σ subunit can be specifically controlled for use in screening methods. Moreover, there is a need in the art for specific methods and compositions that allow the identification of antimicrobial agents which interact with and/or modify the function of the RNA polymerase σ subunit thereby inhibiting bacterial growth.

SUMMARY OF THE INVENTION

Accordingly, it is an object of the present invention to provide an organism in which the production of an RNA polymerase specificity factor can be controlled.

It is a further object of the present invention to provide a recombinant organism having a regulatable gene which encodes an RNA polymerase specificity factor required for expression of a gene or set of genes essential for growth or continued existence of the organism.

It is still a further object of the present invention to provide a method for producing such a recombinant organism.

It is another object of the present invention to provide a staphylococcal bacterial strain in which the production of RNA polymerase a subunit can be controlled.

It is still another object of the present invention to provide an engineered staphylococcal bacterial strain which allows the identification of antimicrobial agents that interact with the function of the RNA polymerase σ subunit thereof.

Yet another object of the present invention is to provide a method for high throughput screening to detect candidate antimicrobial compounds useful against certain organisms, and against staphylococcal bacterial strains in particular.

Still another object of the present invention is to provide a method of profiling drug susceptibilities of S. aureus carrying an inducible gene for expressing RNA polymerase σ factor.

According to the present invention then, a recombinant organism is provided which has a regulatable gene for encoding an RNA polymerase specificity factor required for expression of a selected gene essential for growth of the organism. In particular, the recombinant organism may be a recombinant bacterial strain wherein the regulatable gene is an inducer-responsive gene including an operator site to which a repressor is capable of binding either completely or incompletely thereby to repress gene transcription of the RNA polymerase specificity factor.

More specifically, the present invention is directed to a recombinant staphylococcal bacterial strain which has a regulatable gene for encoding staphylococcal RNA polymerase σ subunit required for expression of selected housekeeping genes relating to growth of the staphylococcal bacterial strain. In particular, the regulatable gene may include a lac operator with which a lacI-encoded repressor is capable of binding either completely or incompletely thereby to repress gene transcription of the RNA polymerase σ subunit. The regulatable gene is preferably an IPTG responsive plaC allele, and the recombinant staphylococcal bacterial strain is preferably a S. aureus strain.

The present invention is also directed to a method for producing a recombinant organism having a regulatable gene for encoding an RNA polymerase specificity factor required for expression of a selected gene essential for growth or continued existence of the organism. The method includes the steps of identifying a wild-type gene encoding the RNA polymerase specificity factor, generating target gene fragments thereof which lack native transcriptional control sequences, and ligating the target gene fragments into an appropriate integrative vector at a location downstream of an inducible promoter. The integrative vector is then integrated into a chromosome of a wild-type organism to produce the recombinant organism. The integrative vector may specifically include a repressor-encoding gene, a resistance determinant, a multicloning site for insertion of the target gene fragment and a transcription terminator.

In particular, the method is directed to producing a recombinant staphylococcal bacterial strain, such as a strain of S. aureus, which has a regulatable gene for encoding RNA polymerase σ subunit. The wild-type gene is preferably plaC, and the integrative vector preferably is a plasmid which includes a lacI gene for encoding a repressor, a multicloning site preferably including an SrfI site for insertion of the target gene fragments, a transcription terminator, and a chloramphenicol resistance determinant.

A further embodiment of the invention relates to a method for high throughput screening to identify candidate pharmaceutical compounds that are effective against an organism, such as staphylococcal bacterial strains and S. aureus in particular. In particular, the method identifies candidate pharmaceutical compounds that target an RNA polymerase specificity factor, such as the σ factor in S. aureus, required for expression of at least one gene essential for continued existence, e.g., growth and/or viability, of the organism. The method comprises the steps of preparing a plurality of cultures, contacting each of the cultures with a test compound, and monitoring the cultures to detect results indicating that the test compound targets the RNA polymerase specificity factor. The step of preparing a plurality of cultures includes preparing cultures of a first type and a second type. The first type of cultures includes a recombinant strain of the organism that has a regulatable gene for encoding the RNA polymerase specificity factor, whereas the second type of cultures include a wild-type strain of the organism that has a wild-type gene for encoding the RNA polymerase specificity factor. The regulatable gene may be one which is regulated by various methods, such as the use of repressor and inducer molecules as known in the art. The regulatable gene is expressed at basal levels in some of the cultures of the first type, and the regulatable gene is expressed at above basal levels in others of the cultures of the first type as a result of exposure of some of the cultures of the first type to an exogenous effector molecule, such as a gene inducing agent or a repressor molecule initiator as determined by the regulatory condition of the regulatable gene. Some of the cultures of the second type are also exposed to the exogenous effector molecule.

When a gene inducing agent is added as the exogenous effector molecule, the method may include the further step of adding the gene inducing agent in a sub-maximal concentration to those cultures of the first type that were not exposed to the gene inducing agent, if necessary to induce basal level expression of those cultures. Prior to the step of contacting the cultures with the test compound, the cultures are preferably incubated for a selected interval of time under conditions sufficient for growth of each culture to approach a target density. Additionally, after the step of contacting the cultures with the test compound, the cultures are preferably incubated under conditions that support growth of the cultures.

The cultures may be organized into sets and groups which may be organized in an array of columns and rows. Each group is preferably contacted with a different concentration of test compound. The method may be repeated for a plurality of test compounds.

The step of monitoring may be accomplished by measuring the growth of the cultures wherein a test compound that is a candidate pharmaceutical compound inhibits growth of cultures of the first type in which the gene is expressed at basal levels. Alternatively, a candidate pharmaceutical compound may be identified as one that inhibits RNA synthesis in cultures of the first type in which the regulatable gene is expressed at basal levels.

The present invention also relates to a method for high throughput screening to identify candidate pharmaceutical compounds that target an RNA polymerase specificity factor, comprising the steps of preparing a recombinant strain having a regulatable gene for encoding the RNA polymerase specificity factor, growing the strain, isolating and purifiying the RNA polymerase specificity factor, contacting the RNA polymerase specificity factor with a test compound and detecting whether the test compound binds to said RNA polymerase specificity factor.

These and other objects of the present invention will become more readily appreciated and understood from a consideration of the following detailed description of the exemplary embodiments of the present invention when taken together with the accompanying drawings, in which:

BRIEF DESCRIPTION OF THE DRAWINGS

The accompanying drawings which are incorporated in and form a part of the specification illustrate preferred embodiments of the present invention and, together with a description, serve to explain the principles of the invention. In the drawings.

DETAILED DESCRIPTION OF THE EXEMPLARY EMBODIMENTS

Figure 1:
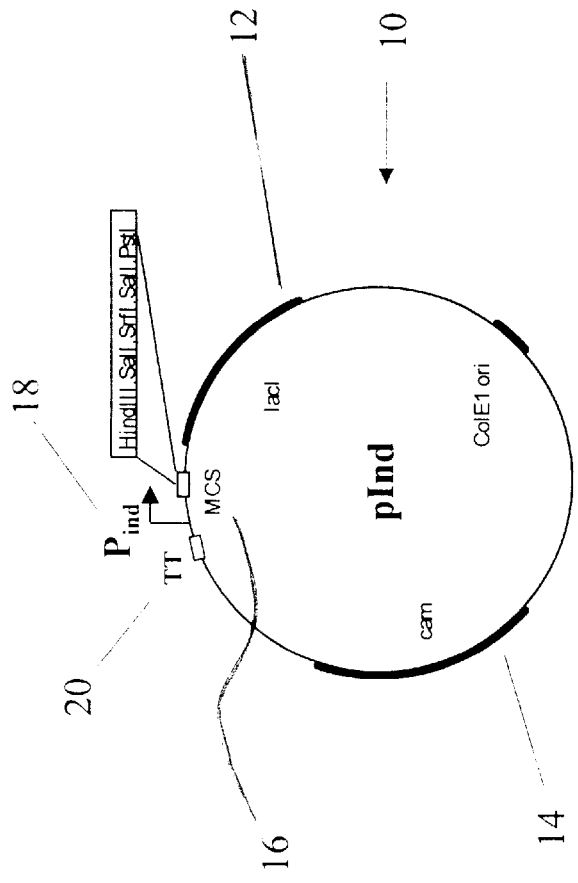
FIG. 1 is a schematic illustration of pInd, an integrative vector used in the present invention to engineer regulated gene expression showing SEQ ID NO:1 and SEQ ID NO:2.

The present invention generally relates to the production of a recombinant organism, specifically a recombinant staphylococcal bacterial strain such as *S. aureus*, and to methods for high throughput screening using the recombinant organism to discover chemical compounds that are pharmaceutically useful against a wild-type organism from which the recombinant organism is derived.

A. Production of the Recombinant Organism

The present invention involves the creation of a recombinant organism in which a native gene is replaced by a genetically engineered gene whose expression can be regulated, such as by the addition of inducer or repressor molecules. The native, or wild-type, gene encodes in the native, or wild-type, organism an RNA polymerase specificity factor which directs binding of the RNA polymerase enzyme to the promoter sequences of a particular gene or set of genes that are essential for growth or continued existence of the organism. By allowing the regulation of RNA polymerase specificity factor production, the recombinant organism provides for external control over the growth and/or continued existence of the organism. Such control permits efficient screening for compounds which show inhibition or blocking of the specificity factor function, which is exhibited by hypersensitivity of the repressed or uninduced recombinant organism to a chemical compound.

It should be appreciated that the specificity factor-encoding genes for use in the recombinant organisms of the present invention may be derived from the wild-type organism, such as a bacterium, and the sequence may be obtained by restriction enzyme digestion of genomic DNA or, preferably, by amplification using a known polymerase chain reaction-based method.

In particular, production of the recombinant organism involves identification of the wild-type gene of interest that encodes an RNA polymerase specificity factor in the native organism and generating target gene fragments thereof which lack native transcriptional control sequences. Preferably, the target gene fragments are generated by polymerase chain reaction (PCR) amplification from wild-type organism genomic DNA. The target gene fragments are then ligated into an appropriate integrative vector at a location downstream of an inducible promoter, such as at a suitable multicloning site (MCS).

The inducible promoter includes an operator from a heterologous regulatory gene. Suitable heterologous regulatory genes include those derived from lac (such as lacl), tet, λ, lex and others as known in the art. The integrative vector preferably includes a repressor-encoding gene corresponding to the chosen regulatory operator, a resistance determinant for selection of the recombinant strain after vector integration, a multicloning site for insertion of the target gene fragment downstream of the inducible promoter, and preferably a bidirectional transcription terminator upstream of the inducible promoter to eliminate read-through transcription.

The integrative vector is then integrated into the DNA of the native organism, such as by electrotransformation. Homologous recombination by selection for the resistance determinant yields recombinant transformants bearing the regulatable gene.

1. Recombinant Staphylococcal Bacterial Strain

In particular, the present invention utilizes a staphylococcus bacterial strain in which a native σ factor-encoding gene, commonly designated as a wild-type gene, has been replaced with a genetically engineered gene whose expression can be induced by the addition of an exogenous effector molecule, and in particular by an inducing agent appropriate to the chosen regulatory operator. In the wild-type *S. aureus* bacterial strain, the RNA polymerase σ subunit required for the expression of the previously mentioned housekeeping genes necessary for bacterial growth and/or viability is produced by the plaC gene within the cell, according to native transcriptional control sequences. With the recombinant staphylococcus bacterial strain of the present invention, however, a regulatable plaC gene is factored into the genetic makeup of the bacterium. This regulatable gene includes an operator site to which a repressor protein may bind, whereby transcription and subsequent expression of the RNA polymerase a subunit is repressed. The repressor protein is produced by an additional gene, such as lacI, within the recombinant DNA.

This repression can be overcome by the addition of an inducer agent which binds with the repressor protein and prevents its repression of the plaC gene, thereby allowing transcription of the plaC gene and expression or production of the RNA polymerase cy subunit. In this manner, the production of RNA polymerase σ subunit within the recombinant Staphylococcus bacterial strain of the present invention can be controlled with the use of inducer agents.

It should be appreciated that the σ factor-encoding genes for use in the recombinant S. aureus bacteria of the present invention include without limitation plaC, sigB and others, and preferably plaC. The σ factor-encoding sequence of the present invention may be derived from any staphylococcal strain, although the preferred bacterium is S. aureus, and the sequence may be obtained by restriction enzyme digestion of genomic DNA or, preferably, by amplification using a known polymerase chain reaction-based method. As noted, suitable heterologous regulatory genes include those derived from lac (such as lacI, tet, λ, lex and others. In preferred form, the regulator gene is lacI which produces the repressor protein that binds to a lac operator in the recombinant plaC gene, thereby suppressing expression of the σ factor.

In constructing the recombinant staphylococcal strains of the present invention, the heterologous promoter-σ factor encoding DNA fragment is encoded in an integrative plasmid vector such as illustrated in FIG. 1. Here, transcription of the plaC gene was placed under the control of an inducible promoter ($P_{ind}$) in S. aureus, wherein $P_{ind}$ includes a lac operator site. In the case of the lac regulator, the preferred inducer or inducing agent for blocking the repression of the promoter is a thiogalactoside and preferably isopropylthiogalactoside (IPTG).

FIG. 1 illustrates a pInd integrative vector, which is a modified version of pAG58 (Jaacks et al., 1989, J. Bacteriol. 171:4121–4129; Henner, 1990, Meth. Enzymol. 185:223–228). pInd 10 carries the lacI regulatory gene 12 which synthesizes the repressor protein for negative regulation of a recombinant gene having a lac operator. pInd 10 also carries a chloramphenicol resistance determinant 14 of plasmid pC194 (Horinouchi & Weisblum, 1982, J. Bacteriol. 150:815–825) which is selectable in Gram-positive bacteria, a multicloning site (MCS) 16 containing a convenient SrfI site for insertion of blunt polymerase chain reaction (PCR) generated target gene fragments downstream of $P_{ind}$ 18, and a bidirectional transcription terminator 20 from bacteriophage φ29 (Barthelemy et al., 1987, J. Virol. 61, No.5:1751–1755) upstream of $P_{ind}$ 18 to eliminate read-through transcripts originating in vector DNA.

Figure 2:
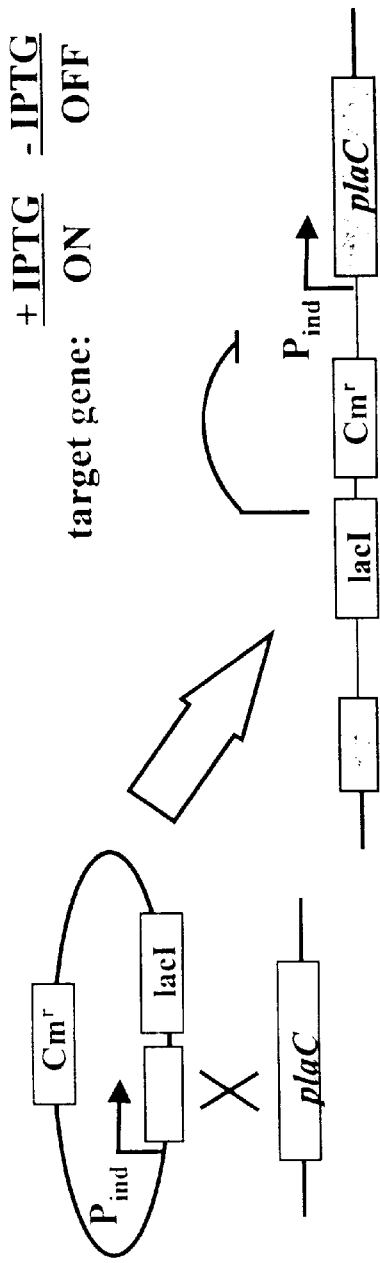
FIG. 2 is a schematic illustrating the construction of *S. aureus* bearing a regulatable plaC gene utilizing an IPTG-inducible promoter.

An IPTG-responsive copy of the plaC gene was engineered in the S. aureus chromosome using a 5'-fragment of plaC cloned into pInd as illustrated in FIG. 2. A 498 bp interval of plaC gene lacking native (i.e. wild-type) transcriptional control sequences was PCR-amplified from 0.1 μg of S. aureus RN4220 (Kreiswirth et al, 1983, Nature 305:709–712) genomic DNA with 1 μg each of primers based on the published plaC sequence (Basheer & Iordanescu, 1991, NAR 19:4921–4924):

5'-ATGTCTGATAACACAGTTAAAATT-3'(SEQ ID NO:3) and

5'-CATATTACCTTCTTGGATTAAATC-3'(SEQ ID NO:4).

The PCR product was ligated into the multi-cloning site of pInd at the SrfI site. The resulting plasmid was integrated into the chromosome of S. aureus RN4220 (Kreiswirth et al, 1983, Nature 305:709–712) at the plaC locus via homologous recombination by selection for plasmid-borne chloramphenicol resistance to yield S. aureus transformants bearing an IPTG-inducible plaC allele, $P_{ind}$-plaC. Electrotransformation of S. aureus was performed as described (Schenk and Laddaga, 1992, FEMS Microbiol. Lett. 94:133–138). Transcription of the engineered $P_{ind}$-plaC gene is induced in response to addition of IPTG to the culture medium. In the absence of IPTG, plaC transcription is repressed by binding of lacI-encoded repressor to an operator site (lacO) near the −10 region of $P_{ind}$ (FIG. 1).

Figure 3:
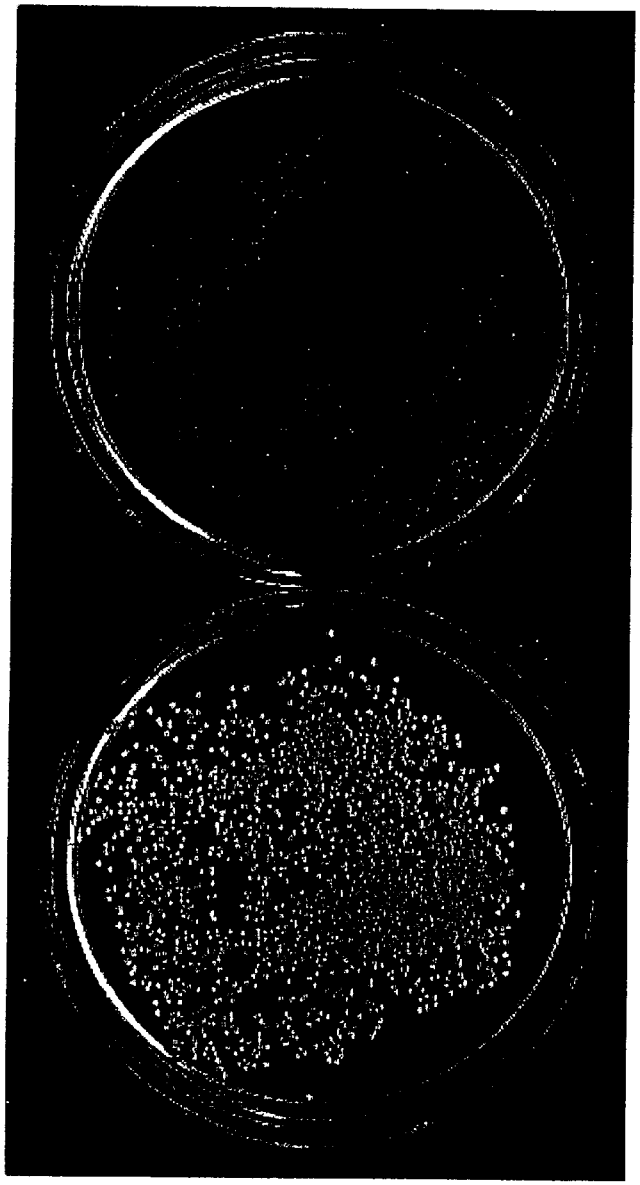
FIG. 3 is a photographic illustration of the growth of the *S. aureus* strains of the invention under inducing and non-inducing conditions.

FIG. 3 shows a phenotypic analysis of S. aureus chloramphenicol-resistant transformants in which plaC transcription has been placed under the control of $P_{ind}$. Bacteria containing $P_{ind}$-plaC were viable in the absence of IPTG and showed pleiotropic phenotypes, including a significant growth defect in comparison with a chloramphenicol-resistant strain which possesses a wild-type plaC allele. In the absence of IPTG, $P_{ind}$-plaC—bearing transformants showed a reduction in colony size and a marked enhancement in the production of yellow carotenoid pigments normally associated with stationary phase, as illustrated in FIG. 3. Further examination of liquid cultures indicated that growth of $P_{ind}$-plaC cells lagged substantially behind that of wild-type cells under non-inducing conditions as clearly illustrated in FIG. 4. Since plaC expression is essential for growth of S. aureus, survival of $P_{ind}$-plaC bacteria in the absence of IPTG is interpreted as resulting from incomplete repression of transmission by lacI, that is "leakiness". Quantitation of plaC levels by immunoblot analysis of cell extracts with anti-plaC antiserum demonstrated induction of plaC expression by IPTG as clearly illustrated in FIG. 5. However, the levels of plaC protein in uninduced cells grown without IPTG (lane 4) were below the limit of detection.

In preferred embodiments of the invention, the integrative vector may be modified to optimize the level of repression of σ-factor expression in the absence of an inducing agent (i.e., −IPTG) as well as to optimize the induction of σ-factor expression in the presence of an inducing agent (i.e., +IPTG). Such modifications, which are within the scope of the invention, include without limitation the inclusion of additional control sequences such as operator sites and transcription termination sites.

It should be understood that transformation of a staphylococcal strain, preferably S. aureus, with a plaC containing integrative plasmid may be achieved using any method known in the art, preferably by electroporation. Recombination between plasmid-derived sequences and genomic DNA results in replacement of the native σ factor-encoding gene (i.e., the wild-type) with the recombinant gene present in the plasmid. Expression of the σ subunit in the recombinant strain of the invention can be induced using the inducing agent (or effector molecule) specified by the heterologous promoter. For example, when lac is used, expression of the σ factor can be induced by exposing the bacterial culture to IPTG which, as previously indicated, binds to the lacI repressor protein and reverses or blocks the gene repression.

An exemplary recombinant S. aureus strain according to the present invention is on deposit with ATCC as a patent deposit. The culture was deposited on Dec. 1, 1999 with American Type Culture Collection, ATCC Patent Depository, 10801 University Blvd., Manassas, Va. 20110-2209, which was designated *Staphylococcus aureus* RN4220, SP101 and assigned accession number PTA-1007 (Reference 1933.02.02.1).

In practicing the present invention, many conventional techniques in molecular biology, microbiology, and recombinant DNA are used. Such techniques are well known and are explained fully in a variety of available texts and articles, the contents of which are specifically incorporated herein by reference, as follows: *Genetics*, by Benjamin Lewin, 1997, Oxford University Press; *Molecular Cloning: A Laboratory Manual*, by Sambrook et al, 1989, Second Edition, Cold Spring Harbor Laboratory Press, Cold Spring Harbor, New York; *DNA Cloning: A Practical Approach*, Volumes I and II, 1985, (D. N. Glover ed.); *Oligonucleotide Synthesis*, 1984, (M. L. Gait,ed.); *Nucleic Acid Hybridization*, 1985, (Hames & Higgins, eds.); *Transcription and Translation*, 1984, (Hames & Higgins, eds.); *Animal Cell Culture*, 1986, (R. I. Freshney, ed.); *Immobilized Cells and Enzymes*, 1986 (IRL Press); *A Practical Guide to Molecular Cloning*, 1984, by Perbal; *Methods in Enzymology*, the series (Academic Press, Inc.); *Gene Transfer Vectors for Mammalian Cells*, 1987 (J. H. Miller and M. P. Calos, eds., Cold Spring Harbor Laboratory); *Methods in Enzymology*, Vols. 154,155 (Wu and Grossman, eds.); and *Guide to Yeast Genetics and Molecular Biology, Meth. Enzymol*, Vol. 194 (Guthrie and Fink, eds.).

The present invention also provides isolated staphylococcal RNA polymerase cy factor for use in screening methods to identify antimicrobial compounds through the controlled production of RNA polymerase σ subunit with the *S. aureus* bacterial strain of the invention. According to the invention, σ factor polypeptides are preferably at least five or more residues in length. Preferably, the polypeptides comprise at least 12, more preferably at least about 20, and most preferably at least about 30 such residues, up to and including the complete amino acid sequence of the protein. Many conventional techniques in protein biochemistry and immunology may be used in the invention to obtain these polypeptides.

In particular, the polypeptides of the invention, including function-conservative variants of staphylococcal RNA polymerase σ subunits, may be isolated from wild-type, mutant or recombinant cells, or from heterogenous cells or organisms. Moreover, the polypeptides may be chemically synthesized by commercially available, known procedures such as exclusive solid phase synthesis, partial solid phase methods, fragment condensation, or classical solution synthesis. Finally, methods for polypeptide purification are well-known in the art, and isolated polypeptides may be modified by, for example, phosphorylation, sulfation, acylation, or other known protein modifications. They may also be modified with a gel label capable of providing a detectable signal including radioisotopes and fluorescent compounds.

B. Screening Methods

The present invention also provides methods for identifying pharmaceutically suitable antimicrobial compounds that act by inhibiting the function of an RNA polymerase specificity factor, such as the RNA polymerase cy subunit in *S. aureus*. It should be appreciated that the screening methods of the present invention may be practiced with other organisms of interest to identify candidate pharmaceutical or antimicrobial compounds that inhibit the function of an RNA polymerase specificity factor required for expression of housekeeping gene(s) essential for growth and/or viability of an organism.

The exemplary method of the invention includes preparing and incubating parallel cultures of induced and uninduced recombinant and wild-type staphylococcal strains, preferably *S. aureus*. Minimal expression of RNA polymerase σ subunit in an uninduced recombinant strain, as a result of incomplete binding of a repressor to the regulatory gene's operator site, results in hypersensitivity of the uninduced recombinant strain to test comounds which target the σ subunit. This hypersensitivity is indicated by limited growth of the uninduced recombinant strain relative to the other strains when all are in the presence of a test compound that targets the σ subunit. While the preferred embodiments of the invention described below utilize the *S. aureus* bacterial strain, it should be understood that the present invention is applicable to any type of staphylococcal bacterial strain. Further, it should be understood that the general screening method of the invention may further be practiced with any recombinant organism in which the production of an RNA polymerase specificity factor is regulatable. Additionally, it should be understood that the screening method of the invention may be modified, to the extent understood by the ordinarily skilled person, to accommodate the use of different regulatory mechanisms.

Figure 6:
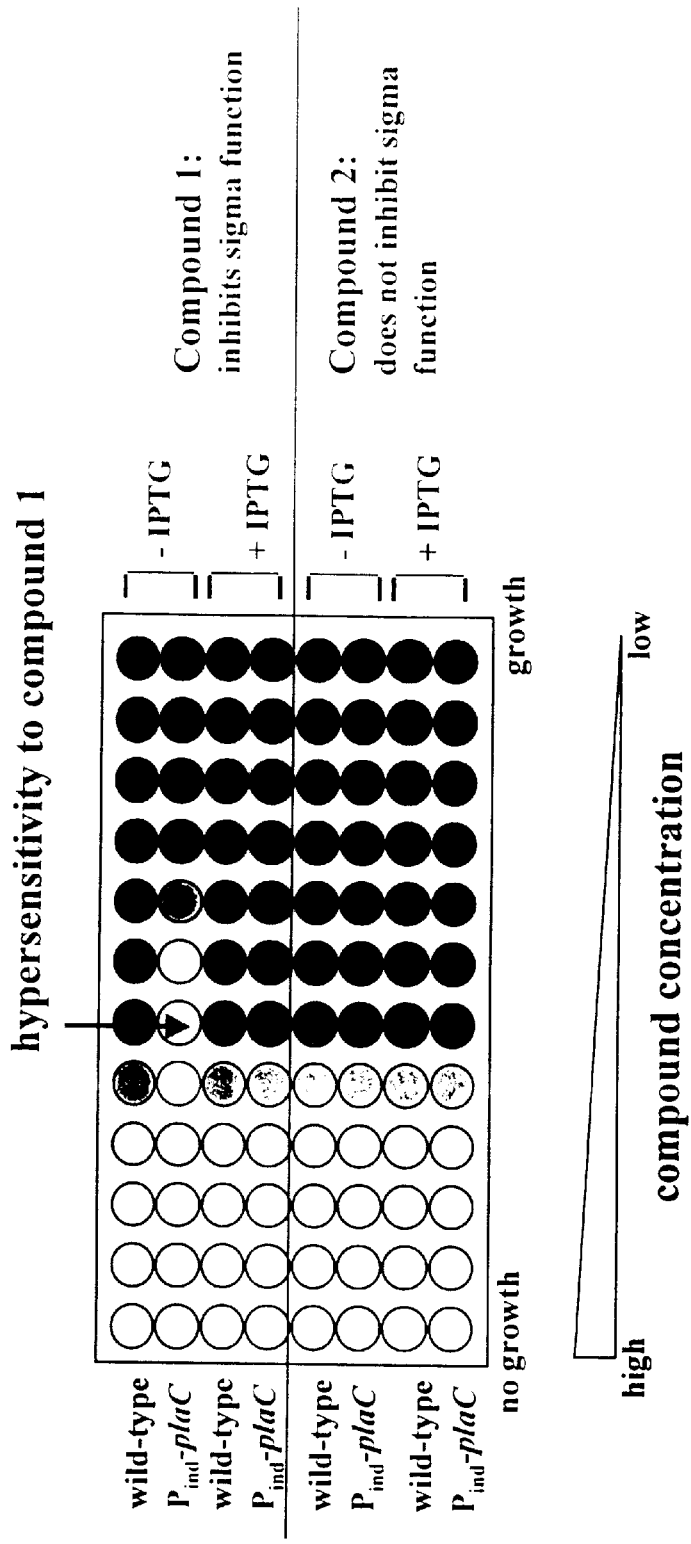
FIG. 6 is a schematic illustrating the profiling of drug susceptibilities of *S. aureus* bearing an IPTG-inducible plaC gene.

In accordance with the exemplary method of the invention, a plurality of cultures is prepared using known techniques and preferably organized in an array, or grid, format. An exemplary organization of such cultures is illustrated in FIG. 6, such as the array shown for Compound 1 or for Compound 2. A plurality of cultures of a first type and a plurality of cultures of a second type is prepared. The cultures of the first type include a recombinant *S. aureus* strain having a negatively regulated, inducer-responsive plaC gene for encoding staphylococcal RNA polymerase σ subunit. The cultures of the first type are indicated as "$P_{ind}$-plaC" in FIG. 6. The cultures of the second type include an *S. aureus* bacterial strain having a wild-type gene for encoding the RNA polymerase σ subunit. In FIG. 6, the cultures of the second type are indicated as "wild-type". In FIG. 6, the plurality of cultures are shown in an array form for example for Compound 1 on the top and for Compound 2 on the bottom. It should be appreciated, however, that the organization of the cultures may be modified as understood in the art.

Some of the cultures of the first type and some of the cultures of the second type are exposed to an exogenous effector molecule, such as an inducer or repressor molecule, as appropriate to the chosen regulatory operator in the recombinant strain. Preferably, the exogenous effector molecule is added to fewer than all of the cultures of the first type and fewer than all of the cultures of the second type. More preferably, the exogenous effector molecule is added to half of the cultures of the first type and half of the cultures of the second type.

In the exemplary embodiment, as shown in FIG. 6, the cultures are preferably organized into a first set and a second set of cultures of the first type and a third set and a fourth set of cultures of the second type. The effector molecule is preferably a gene inducing agent, preferably IPTG, added to the first set, preferably half of the $P_{ind}$-plaC cultures, thereby to induce expression of the regulatable gene in the cultures to which IPTG is added. The effector molecule is also added to the third set, preferably half of the second type of cultures. Cultures to which IPTG has been added are indicated in FIG. 6 by "+IPTG", and cultures to which IPTG has not been added are indicated by "−IPTG". Consequently, there are four sets of parallel cultures which make up the array, specifically wild-type +IPTG, wild-type −IPTG, $P_{ind}$-plaC recombinant +IPTG, and $P_{ind}$-plaC recombinant −IPTG. FIG. 6 illustrates these sets of cultures aligned in horizontal rows.

In the $P_{ind}$-plaC recombinant −IPTG cultures, the regulatable gene is expressed at basal levels, just sufficient to support growth of the organism, as a result of the incomplete repression of transmission, or "leakiness" of the regulatory system, discussed above. In the $P_{ind}$-plaC recombinant +IPTG cultures, the regulatable gene is expressed at above basal levels as a result of the induction of expression by IPTG. In the wild-type cultures, the regulatable gene is expressed according to native transcriptional control sequences, preferably at above basal levels. Accordingly, the $P_{ind}$-plaC recombinant −IPTG cultures are expected to display hypersensitivity to test compounds that target RNA polymerase σ subunit, as a result of the limited amount of RNA polymerase σ subunit present in the $P_{ind}$-plaC recombinant −IPTG cultures.

It should be understood that in some cases, generally dependant upon the type of organism and the type of regulatory system, the "leakiness" of the uninduced recombinant set may be insufficient to support minimal growth of the organism, in which case addition of the inducing agent to the uninduced recombinant set in sub-maximal levels may be necessary. Further, it should be understood that the present method may be adapted to organisms having regulatable genes which are expressed in the absence of a repressor. In such cases, it may be necessary to add the repressor to some of the recombinant cultures in an amount sufficient to repress expression of the regulatable gene to basal levels, sufficient to support only limited growth of the organism. Cultures to which the repressor is not added should be expressed at above these basal levels.

Figure 4:
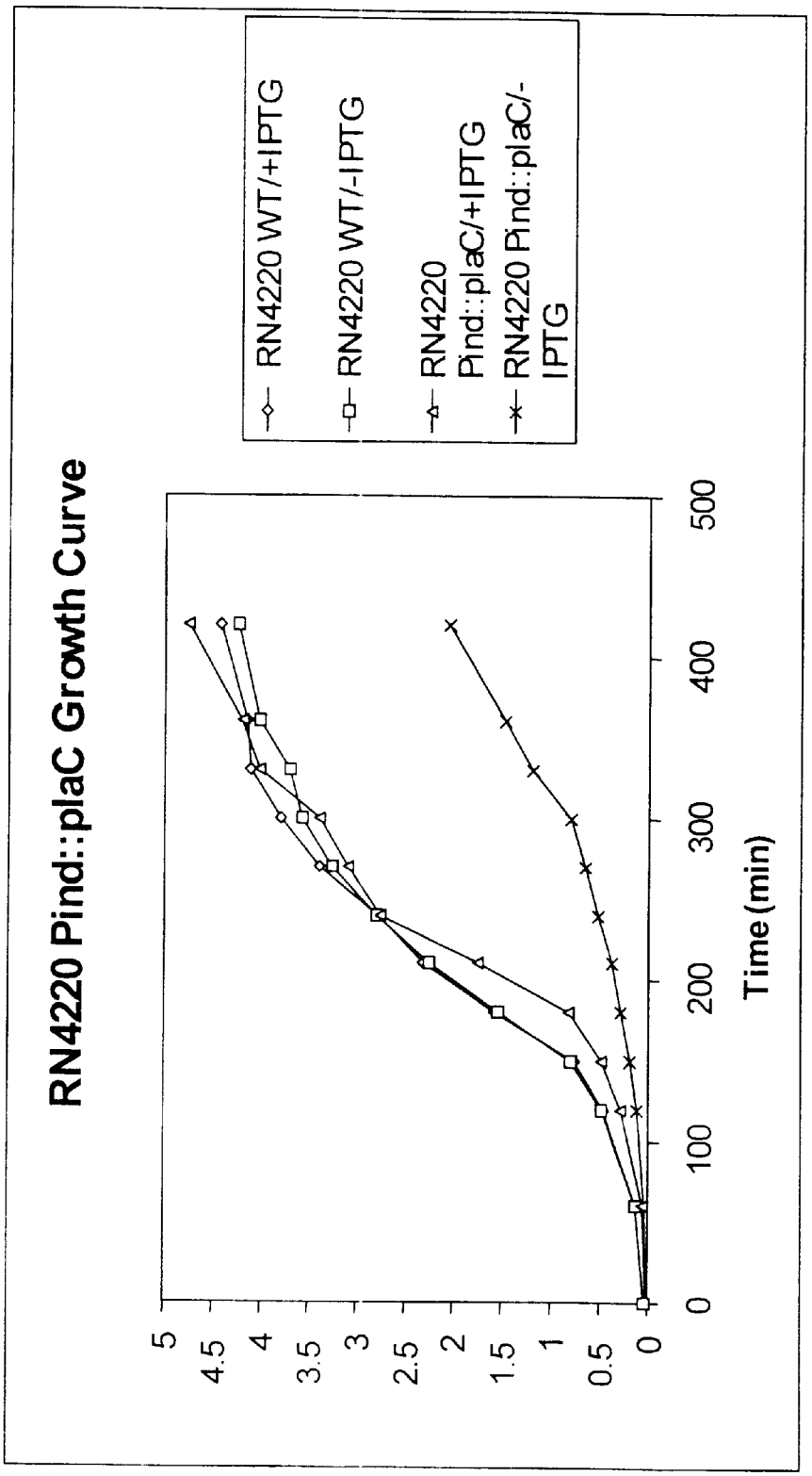
FIG. 4 is a graphic illustration of the growth of wild-type *S. aureus* strains and modified *S. aureus* strains engineered in accordance with the present invention, under growth conditions that both include and exclude the presence of gene inducing agent IPTG.
Figure 5:
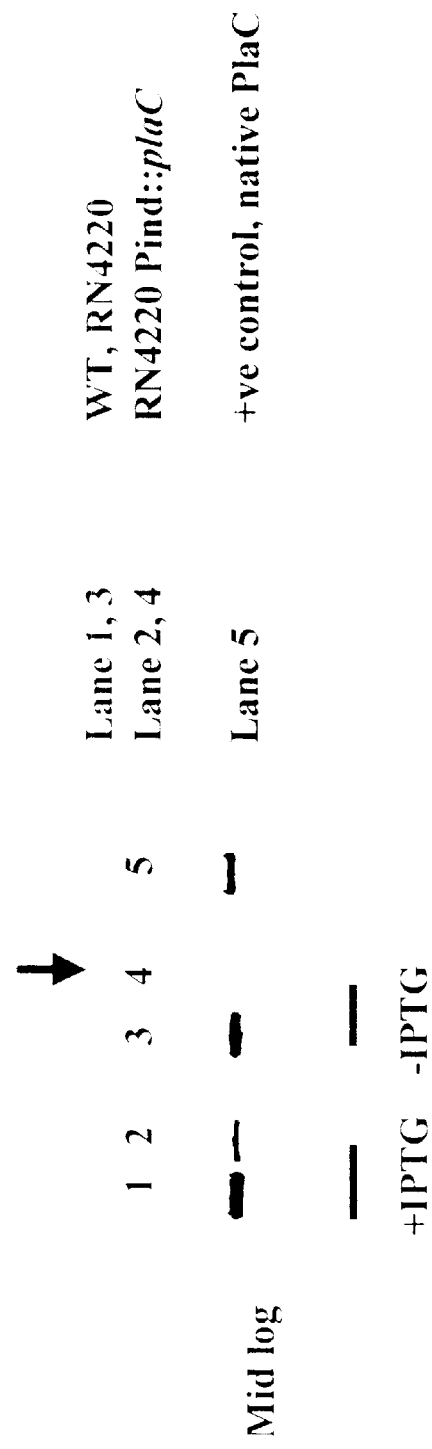
FIG. 5 is a photographic illustration of an immunoblot analysis of cell extracts illustrating quantitation of plaC expression by IPTG.

Preferably, the cultures are then incubated for an interval of time, preferably overnight, sufficient for the density of the cultures to approach a target density, for example a density that is similar in all cultures, such that the initial slower expected growth of the $P_{ind}$-plaC recombinant −IPTG set, as demonstrated in FIG. 4, is not a factor.

The cultures are then contacted with a test compound, and are preferably incubated under conditions which would normally support the growth of all the cultures incubated in the absence of the test compounds. As shown in FIG. 6, it is unexpected that hypersensitivity of the uninduced recombinant culture ($P_{ind}$-plaC recombinant −IPTG) to a test compound which targets σ subunit will be observed at either very high or very low concentrations of test compound. Accordingly, it is preferred that the plurality of cultures be further divided into groups, wherein each group includes one culture from each of the sets, as shown by the vertical columns of cultures in FIG. 6. It is further preferred that each group is contacted with the test compound in a different concentration from the other groups, as shown by the decreasing concentration of test compound from left to right in the cultures in FIG. 6. Accordingly, the respective sets of cultures each preferably receive a range of concentrations of test compound over which the effect of the compound on the cultures may be monitored for indications that the test compound is a candidate pharmaceutical compound. It should be understood that if a given concentration of interest is identified, each set need only include one culture, rather than a plurality of cultures, wherein the test compound is added at the given concentration.

The cultures contacted with the test compound are then monitored for indications that the test compound is a candidate pharmaceutical compound effective against the organism. For example, bacterial growth in the cultures may be measured. A test compound having antimicrobial capability by inhibiting σ factor function may be identified as one that inhibits bacterial growth in the uninduced recombinant set, e.g. $P_{ind}$-plaC recombinant −IPTG, relative to the remaining sets of cultures at a selected concentration of test compound. Moreover, inhibition of RNA synthesis or production may also be determined in the cultures, wherein a test compound is identified as a candidate when the test compound inhibits RNA synthesis in the $P_{ind}$-plaC recombinant −IPTG set relative to the remaining sets of cultures. Both the growth of the cultures and the RNA synthesis may be measured using any desired conventional techniques. For example, growth may be measured by monitoring absorbance of the culture in, for example, a Klett reader or spectrophotometer. RNA synthesis may be measured, for example, by measuring incorporation of a radiolabeled RNA precursor, or by monitoring the expression of a reporter gene whose transcription is controlled by a σ-dependent promoter.

Compounds that inhibit the growth and/or inhibit RNA synthesis of the uninduced recombinant set relative to the remaining cultures are candidate antibacterial agents, because these compounds clearly inhibit or at least interfere with the low level of transcription of the RNA polymerase σ factor displayed in the uninduced recombinant set. That is, in the case of the exemplary plaC gene of S. aureus, the repressor binds the IPTG-responsive plaC gene incompletely such that even in the absence of the IPTG inducer agent, (−IPTG), the plaC gene is still transcribed at very low basal levels to form limited amounts of RNA polymerase σ subunit resulting in limited growth. Thus, the cultures without the inducer ($P_{ind}$-plaC recombinant −IPTG) are highly susceptible, or hypersensitive, to antimicrobial compounds which target σ subunit expression relative to the wild-type bacterial strains or the induced recombinant strains, since there is little σ subunit production to begin with in the uninduced recombinant set. In the case of other genes and organisms of interest, the recombinant set may produce insufficient specificity factor in the absence of the inducer to result in any growth. In such instances, to the extent understood by the ordinarily skilled person, it may be necessary to add sub-maximal levels of the inducer thereby to induce limited specificity factor production resulting in limited growth whereby such cultures would become similarly hypersensitive to compounds targeting the specificity factor.

The method of the present invention offers advantages in applications pertinent to drug discovery and drug profiling. In this particular example, S. aureus cells bearing $P_{ind}$-plaC were used to develop cell based screens for chemical compounds which inhibit the function of σ. The phenotype of $P_{ind}$-plaC bearing S. aureus grown without IPTG is formally similar to that produced by a temperature sensitive plaC mutant grown under semi-permissive conditions. Such bacteria can be viewed as possessing attenuated or lessened σ function. It is anticipated that in the absence of IPTG, $P_{ind}$-plaC bacteria shows heightened susceptibility to molecules which target a relative to bacteria which have a wild-type plaC gene as illustrated in FIG. 6.

In another embodiment, $P_{ind}$-plaC S. aureus should prove useful in drug profiling studies aimed at establishing the intracellular target of a lead compound with antibacterial activity, particularly in cases in which the compound has been identified initially using functional assays for in vitro inhibitors of S. aureus RNA polymerase.

In yet another embodiment of the present invention, useful candidate pharmaceutical compounds, and anti-S.

aureus compounds in particular, are identified as those which specifically bind to RNA polymerase specificity factor, which in the case of *S. aureues* is the plaC gene product, i.e. RNA polymerase σ subunit. The inducible strains of the present invention, and in particular $P_{ind}$-plaC recombinant+IPTG, can be used to provide large amounts of the RNA polymerase σ subunit by preparing and growing cultures under conditions in which the regulatable gene is expressed, such as by addition of the IPTG inducing agent. This can be purified and then used in in vitro assays. Typically, these assays include contacting the plurality of test compounds with the purified staphylococcal RNA polymerase σ subunit, and then measuring the binding of the test compounds to the σ factor. Such binding may be measured using any means known in the art, such as those disclosed in the aforementioned U.S. Pat. Nos. 5,585,277 and 5,679,582 to Bowie et al. It should be understood that the present invention may also be useful in other assay techniques, such as functional assays.

Preferably, the screening methods of the present invention are adapted for use with a plurality of test compounds, such as in a high-throughput format, allowing a multiplicity of compounds to be analyzed in a single assay. Such inhibitory compounds may be found in, for example, naturally occurring libraries, fermentation libraries encompassing plants and microorganisms, compound files, and synthetic compound libraries. Such compound libraries are commercially available from a number of known sources. The compounds identified using the methods of the present invention discussed above may be modified to enhance potency, efficacy, uptake, stability and suitability for use in pharmaceutical formulations and the like. These modifications are achieved and tested using methods well-known in the art.

As can be seen from the above, the system of the present invention is designed for regulated gene expression in staphylococcal bacteria, and in particular *S. aureus*. The present invention was devised for the purpose of analyzing essential genes and for assessing the role of target gene products in bacterial growth and viability. The present invention involves the creation of a recombinant staphylococcus bacterial strain in which a native σ factor-encoding gene has been replaced with a genetically engineered gene whose expression can be induced by the addition of an exogenous effector molecule, and in particular IPTG. Moreover, methods are presented for determining pharmaceutically effective staphylococcus bacteria antimicrobial candidates using the engineered *S. aureus* strain of the invention.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A recombinant organism having a regulatable gene encoding an RNA polymerase specificity factor required for expression of at least one gene essential for growth of said organism, wherein said organism is a Staphylococcus bacterial-strain, and wherein said regulatable gene is responsive to an exogenous effector molecule.

2. A recombinant organism according to claim 1 wherein said bacterial strain is a *Staphylococcus aureus* strain.

3. A recombinant organism having a regulatable gene encoding an RNA polymerase specificity factor required for expression of at least one gene essential for growth of said organism, wherein said organism is a Staphylococcus bacterial cell, said regulatable gene is responsive to an exogenous effector molecule, and wherein said regulatable gene is an inducer-responsive gene including an operator site to which a repressor is capable of binding.

4. A recombinant staphlococcal bacterial cell having a regulatable gene encoding a staphlococcal RNA polymerase σ subunit required for expression of at least one gene essential for growth of said staphlococcal bacterial strain, wherein said regulatable gene is responsive to an exogenous effector molecule.

5. A recombinant staphylococcal bacterial strain according to claim 4 wherein said regulatable gene is an inducer-responsive gene including an operator site to which a repressor is capable of binding.

6. A recombinant staphylococcal bacterial strain according to claim 5 wherein said repressor is capable of binding to said operator site incompletely with respect to the mechanics of said repressor binding to said operator site and with respect to the completeness with which said repressor inactivates expression of said σ subunit.

7. A recombinant staphylococcal bacterial strain according to claim 5 wherein said operator site is a lac operator and said repressor is a lacI-encoded repressor.

8. A recombinant staphylococcal bacterial strain according to claim 4 wherein said regulatable gene is a placC allele.

9. A recombinant staphylococcal bacterial strain according to claim 8 wherein said regulatable gene is an IPTG responsive placC allele and wherein said strain includes a lacI gene encoding a repressor that is capable of binding to said IPTG responsive placC allele at a lac operator site.

10. A recombinant staphylococcal bacterial strain according to claim 9 wherein IPTG is operative to prevent said repressor from repressing transcription of said IPTG responsive placC allele.

11. A recombinant staphylococcal bacterial stain according to claim 9 wherein said repressor binds said lac operator site incompletely.

12. A recombinant staphylococcal bacterial strain according to claim 9 wherein said bacterial strain is a recombinant *Staphylococcus aureus* strain.

13. A recombinant staphylococcal bacterial strain according to claim 4 wherein said bacterial strain is a recombinant *Staphylococcus aureus* strain.

14. The recombinant *Staphylococcus aureus* strain RN4220, SP101.

* * * * *

SEQUENCE LISTING

<160> NUMBER OF SEQ ID NOS: 4

<210> SEQ ID NO 1
<211> LENGTH: 56
<212> TYPE: DNA
<213> ORGANISM: Plasmid pAG58

<400> SEQUENCE: 1
ttgactttat ctacaaggtg tggcataatg tgtggaattg tgagcggata acaatt          56

<210> SEQ ID NO 2
<211> LENGTH: 54
<212> TYPE: DNA
<213> ORGANISM: Plasmid pAG58

<400> SEQUENCE: 2
aagcttaagg aggtgatcta gagtcgacgc ccgggcgtcg acctgcaggc atgc            54

<210> SEQ ID NO 3
<211> LENGTH: 24
<212> TYPE: DNA
<213> ORGANISM: Staphylococcus aureus

<400> SEQUENCE: 3
atgtctgata acacagttaa aatt                                            24

<210> SEQ ID NO 4
<211> LENGTH: 24
<212> TYPE: DNA
<213> ORGANISM: Staphylococcus aureus

<400> SEQUENCE: 4
catattacct tcttggatta aatc                                            24